United States Patent
Arai et al.

[11] Patent Number: 5,889,370
[45] Date of Patent: Mar. 30, 1999

[54] STRUCTURE FOR ELIMINATING NOISE IN LIGHT SOURCE DEVICE FOR ELECTRONIC ENDOSCOPE

[75] Inventors: Kaoru Arai; Shigeo Suzuki, both of Omiya, Japan

[73] Assignee: Fuji Photo Optical Co., Ltd., Omiya, Japan

[21] Appl. No.: 827,104

[22] Filed: Mar. 17, 1997

[30] Foreign Application Priority Data

| Mar. 22, 1996 | [JP] | Japan | 8-093330 |
| Mar. 22, 1996 | [JP] | Japan | 8-093331 |
| Mar. 22, 1996 | [JP] | Japan | 8-093332 |

[51] Int. Cl.$^6$ ............................... H04N 7/18; A61B 1/00
[52] U.S. Cl. ........................ 315/85; 315/57; 315/248; 348/65; 348/75; 358/98; 358/160
[58] Field of Search ............................... 315/85, 248, 57; 348/65, 75; 358/98, 160

[56] References Cited

U.S. PATENT DOCUMENTS

| 4,849,950 | 7/1989 | Sugiura et al. | 363/48 |
| 4,864,194 | 9/1989 | Kobayashi et al. | 315/248 |
| 5,220,298 | 6/1993 | Nagase | 333/185 |
| 5,528,205 | 6/1996 | Wong | 333/177 |
| 5,543,831 | 8/1996 | Tsuji et al. | 348/65 |

*Primary Examiner*—Don Wong
*Assistant Examiner*—Wilson Lee
*Attorney, Agent, or Firm*—Ronald R. Snider

[57] ABSTRACT

A structure for eliminating the noise in a light source device for an electronic endoscope safely eliminates the high-frequency noise produced from the lighting circuit, the xenon lamp and the like in the light source device. A capacitor for eliminating noise having a predetermined withstand voltage is connected between the support of the lighting circuit and the box body of the light source device so as to introduce the noise current produced by the switching operation of the lighting circuit to the ground. EMI springs are disposed between the outer peripheral surface of the conductive case of the lighting circuit and the xenon lamp and the inter peripheral surface of the box body of the light source device. A ferrite core for eliminating noise is provided on a conductive wire connecting the lighting circuit and the xenon lamp, thereby safely eliminating noise.

6 Claims, 7 Drawing Sheets

STRUCTURE FOR ELIMINATING NOISE IN LIGHT SOURCE DEVICE FOR ELECTRONIC ENDOSCOPE

BACKGROUND OF THE INVENTION

This application claims the priority of Japanese Patent Applications Nos. 8-93330, 8-93331 and 8-93332 filed on Mar. 22, 1996 which are incorporated herein by reference.

1. Field of the Invention

The present invention relates to a light source device for an electronic endoscope and, more particularly, to a structure for eliminating the noise produced in a light source device which controls the lighting operation of a xenon lamp.

2. Description of the Related Art

Electronic endoscopes are intraperitoneal mirrors for picking up an image of a body cavity as an object of observation by a CCD, which is a charged coupled device disposed at the end portion of an electronic endoscope. Light for irradiating the body cavity is supplied through a light guide disposed from a light source device to the end portion.

Figure 10:
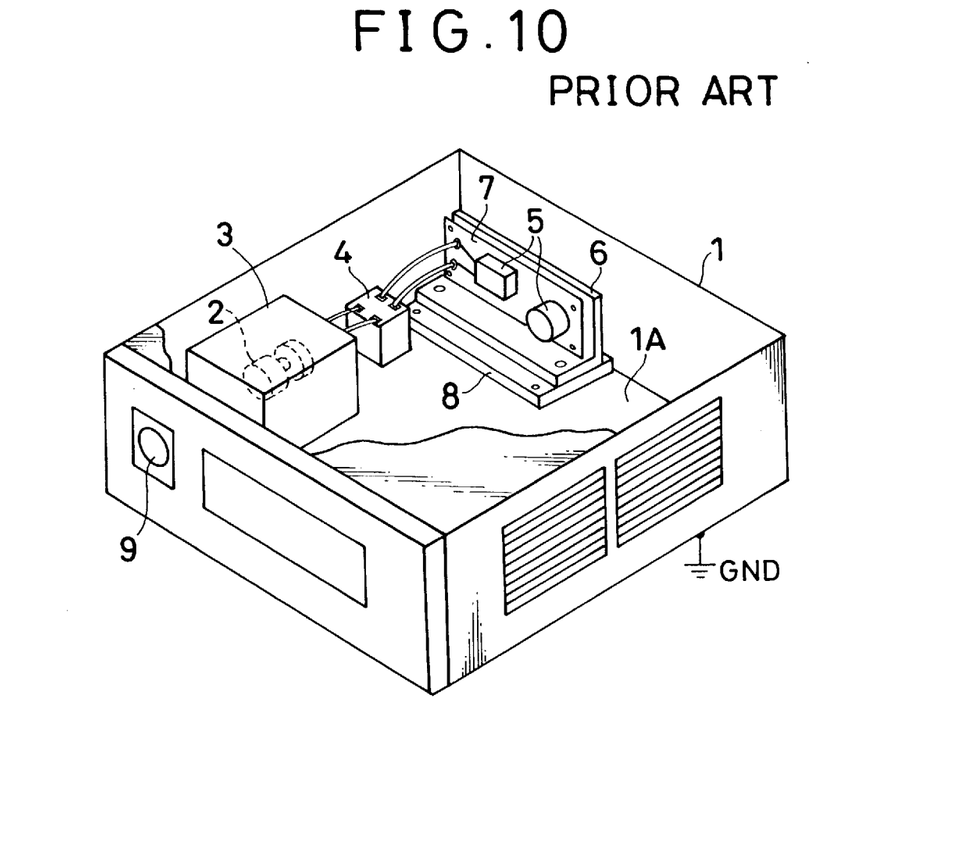
FIG. 10 is a perspective view of the structure of a conventional light source device for an electronic endoscope.

FIG. 10 shows the structure of an example of a conventional light source device. A box body 1 is provided therein with a lamp house 3 accommodating a xenon lamp 2, and a lighting circuit 5 connected to the xenon lamp 2 through an igniter 4. The lighting circuit 5 is fixed onto a substrate 7 supported by an L-shaped aluminum support 6, which, in turn, is anchored to a bottom plate 1A of the box body 1 through an insulating plate 8 such as a bakelite sheet.

The insulating plate 8 maintains a withstand voltage of not less than 4 kV between the lighting circuit 5 (e.g., primary) and the box body 1 so as to secure the safety of the box body 1. A connector receptacle 9 for receiving a light guide connector of an electronic endoscope is provided on the front panel of the box body 1, as shown in FIG. 10.

Figure 11:
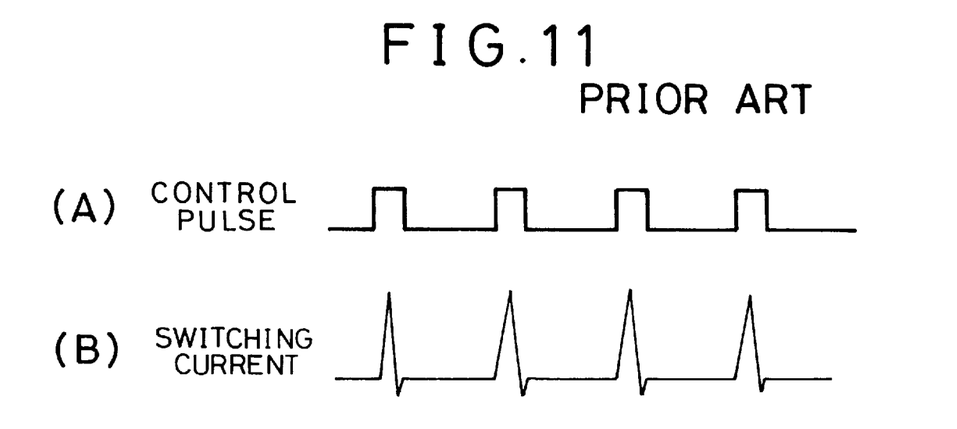
FIG. 11 shows the waveforms of signals used in a light source device.

FIG. 11 shows the waveforms of the signals in the lighting circuit 5. When a switching operation is executed in accordance with the control pulses shown in Fig. 11(A), a switching current having a high frequency such as about 110 kHz is formed, as shown in Fig. 11(B). The switching current is supplied to the igniter 4 shown in FIG. 10, whereby the igniter 4 discharges, and the xenon lamp 2 in the lamp house 3 is lighted. The light of the xenon lamp 2 is supplied to the light guide of the connector of the electronic endoscope which is fitted into the connector receptacle 9, and introduced to the end portion through the light guide, thereby enabling the image pick-up operation of the CCD.

Figure 12:
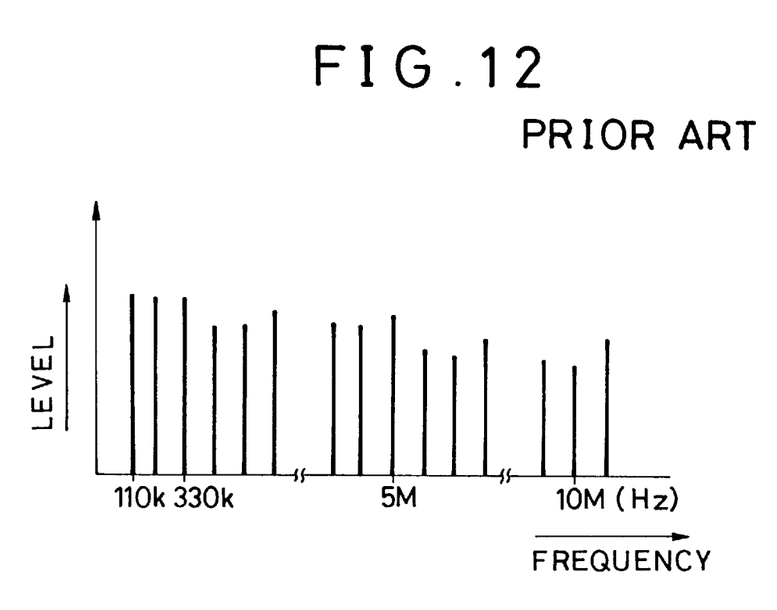
FIG. 12 is a graph of the noise produced in the lighting circuit of a light source device.

According to the above-described light source device, however, the switching current of the lighting circuit 5 produces a high-frequency noise, which exerts a deleterious influence on an image or the like. FIG. 12 shows the noise produced in the lighting circuit 5. As is clear from FIG. 12, since the switching current has a frequency of about 110 kHz, a noise signal having a frequency of an integral multiple of 110 kHz is produced. In addition, since the switching current is comparatively large, the noise maintains a certain degree of level until a high frequency range such as several ten MHz. Since the lighting circuit 5 of the light source device is not in proximity to the processor circuit for processing video signals, no measure against the noise produced in the lighting circuit 5 has been taken in the present state.

Furthermore, a high-frequency noise is also produced due to the discharging operation of the xenon lamp 2, and exerts a deleterious influence on an image or the like. To prevent this, the xenon lamp 2 is accommodated in the metal lamp house 3, which is electrically connected to the box body 1, and a noise current is introduced to the ground so as to prevent the noise produced from the xenon lamp 2 from radiating outward.

However, the electrical connection between the lamp house 3 and the boxy boy 1 is not so good as to certainly maintain the lamp house 3 and the box body 1 at the same potential and to securely eliminate noise. More specifically, the lamp house 3 is connected to the box body 1 by fixing screws and conductive wires on the underside of the lamp house 3. Such a connecting method leaves only a small contact area, which makes it impossible to smoothly introduce the noise current to the ground of the box body.

In addition, the noise component induced to the upper surface of the lamp house 3 is sometimes radiated therefrom before it is led to the ground beneath the lamp house 3, so that it is impossible to completely eliminate such noise.

Furthermore, since a noise current is transmitted to each member through a conductive wire which connects the lighting circuit 5 to the igniter 4 and a conductive wire which connects the igniter 4 to the xenon lamp 2, a noise signal is sometimes produced from such a member in the device.

SUMMARY OF THE INVENTION

Accordingly, it is an object of the present invention to eliminate the above-described problems in the related art and to eliminate the noise produced in a light source device and, more particularly, to provide a structure for eliminating the noise in a light source device for an electronic endoscope which certainly eliminates the high-frequency noise produced in a lighting circuit of a light source and the noise from a xenon lamp or the noise from a conductive wire between the lighting circuit and the light source.

To achieve this end, in one aspect of the present invention, there is provided a structure for eliminating the noise caused from a light source device for an electronic endoscope, the structure comprising: a lighting circuit for controlling the lighting operation of a light source; a box body of the light source apparatus on which a support of the lighting circuit is disposed through an insulating plate; and a capacitor which has a predetermined withstand voltage and which is connected between the support of the lighting circuit and the box body so as to introduce the noise current produced by the switching operation of the lighting circuit from the support of the lighting circuit to the ground of the box body; wherein the support has a substrate and a metal portion.

It is preferable to dispose a shield case body around the outer periphery of the lighting circuit.

In the lighting circuit, since a switching current is used, a noise is induced to and stored in the metal support and particularly, a high-frequency noise is caused from the support. For this reason, a capacitor in which the impedance becomes low when the frequency is 110 kHz to several ten MHz, which is the frequency of the noise produced by the switching current, is used as a capacitor for eliminating noise in the present invention. Therefore, the noise current induced to and stored in the metal support is led to the ground of the box body through the capacitor.

In another aspect of the present invention, there is provided a structure for eliminating the noise in a light source device for an electronic endoscope, the structure comprising: a light source provided with a xenon lamp; a conductive shield case body for accommodating the xenon lamp and/or a lighting circuit for the xenon lamp; and a conductive elastic material inserted between the outer peripheral surface of the shield case body and the inner peripheral surface of the conductive box body of the light source device so as to make electrical contact therewith and maintain the shield case body and the box body at the same potential.

It is preferable that a plurality of the conductive elastic materials are disposed between the upper surface of the shield case body and the back surface of the top plate of the box body.

According to this structure, it is possible to maintain the case body and the box body at the same potential by disposing a plurality of conductive elastic materials such as EMI (Electrro-Magnetic Interference) springs having a large contact area between the upper surface of the shield case body and the back surface of the top plate. It is therefore possible to safely eliminate the noise produced from the xenon lamp and the noise produced from the lighting circuit. Especially by disposing EMI springs on the upper surface, it is possible to safely eliminate the noise which radiates outward.

A structure for eliminating the noise in a light source device for an electronic endoscope provided in a still another aspect of the present invention is characterized in that a ferrite core (magnetic ring) for eliminating noise is provided either on both the wire connecting the anodes and the wire connecting the cathodes of the lighting circuit and the light source or on only the wire connecting the anodes thereof. It is preferable to provide the ferrite cores on the wires on the anode and cathode sides separately.

According to this structure, the noise current transmitted from the lighting circuit to the xenon lamp, which is a light source, through a conductive wire is eliminated by the ferrite core, so that the high-frequency noise produced by the switching current or the igniter discharge current is reduced. Consequently, noise is unlikely to be induced to or stored in the lighting circuit portion, the igniter portion, the light source portion or the like.

The above and other objects, features and advantages of the present invention will become clear from the following description of the preferred embodiments thereof, taken in conjunction with the accompanying drawings.

DESCRIPTION OF THE PREFERRED EMBODIMENT

First Embodiment

Figure 1:
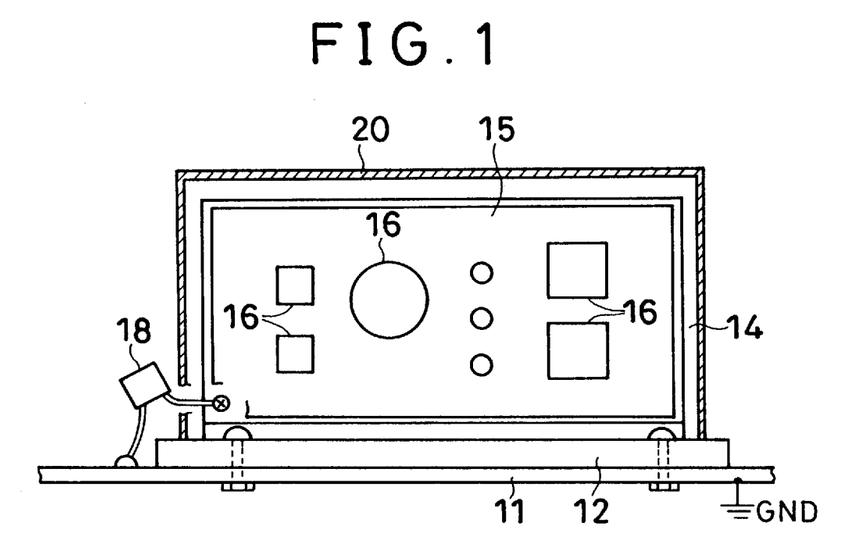
FIG. 1 is an elevational view of a first embodiment of a structure for eliminating the noise in a light source device (lighting circuit portion) for an electronic endoscope according to the present invention.
Figure 2:
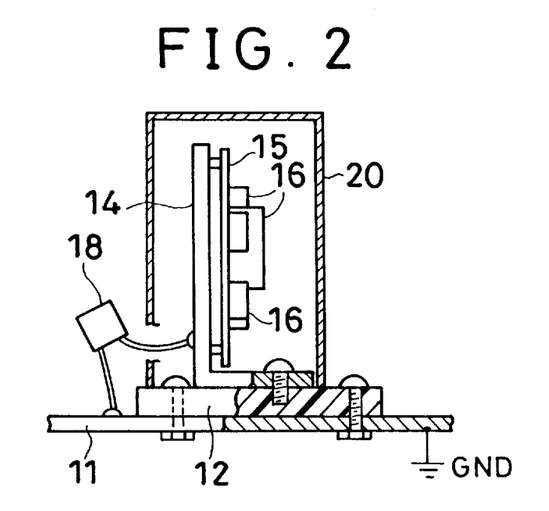
FIG. 2 is a side elevational view of the lighting circuit portion show in FIG. 1.

FIGS. 1 and 2 show a first embodiment of a structure fore eliminating the noise in a light source device for an electronic endoscope according to the present invention. The structure of the light source device is almost the same as the shown in FIG. 10. The structure of the lighting circuit portion will only be explained hereunder. FIG. 1 is an elevational view of the lighting circuit portion and FIG. 2 is a side elevational view thereof. A box body 11 is earthed to the ground (frame ground GND). An insulating plate 12 such as a bakelite sheet is attached to the bottom portion of the box body 11 by fixing screws, and an L-shaped aluminum support 14 is anchored to the insulating plate 12 by fixing screws.

A substrate 15 composed of a bakelite sheet or the like is attached to the support 14 by a screw or the like, and a lighting circuit (composed of a plurality of members) 16 connected to an AC power source is mounted on the substrate 15. A switching circuit such as a transistor is provided in the lighting circuit 16, and the switching current produced thereby is supplied to the xenon lamp 2 through the igniter 4 in the same way as in FIG. 3.

In the lighting circuit 16, a capacitor 18 for eliminating noise is connected between the aluminum support 14 and the box body 11. The structure of the capacitor 18 is not restricted and various kinds of capacitors may be used. The capacitor 18 has a withstand voltage of not less than 4 kV and the impedance thereof becomes low at a frequency of an integral multiple of 110 kHz or not more than several ten MHz. The leg portion (lead wire) of the capacitor 18 is made as short as possible, and the capacitor 18 is directly connected to the support 14 and the box body 11 so as to reduce the impedance component which the leg portion, a fitting metal, etc. have as much as possible.

In this embodiment, not only is the capacitor 18 for eliminating noise connected, the entire part of the support 14 for supporting the substrate 15 of the lighting circuit 16 is covered with a metal shield case body 20 as an electric shielding material. The case body 20 is electrically connected to the support 14 so that the noise current is introduced to the frame ground.

In the light source device o f the first embodiment having the above-described structure, the switching current shown in FIG. 11 which is produced by the lighting circuit 16 is supplied to the igniter 4. The igniter 4 then discharges, thereby lighting the xenon lamp 2. At this time, a noise is produced when the switching current is supplied and the noise current is induced to and stored in the aluminum support 14.

In this embodiment, however, the high-frequency noise current induced to the support 14 is safely caught by the capacitor 18 and led to the ground of the box body 11. Since the support 14, the substrate 15 and the lighting circuit 16 are covered with the case body 20, the noises radiating from the support 14, the lighting circuit 16 and the like are advantageously eliminated, so that they are not leaked outward. The capacitor 18 has a withstand voltage of not less than 4 kV, so that it does not impair the withstand voltage maintained by the insulating plate 12.

As explained above, according to the first embodiment, since a noise current is introduced to the ground of the box body by the capacitor for eliminating noise, it is possible to certainly eliminate the high-frequency noise produced from the lighting circuit. In addition, since the shield case body is provided around the outer periphery of the lighting circuit, the noise radiating the lighting circuit is safely eliminated by the twofold measures.

Second Embodiment

Figure 3:
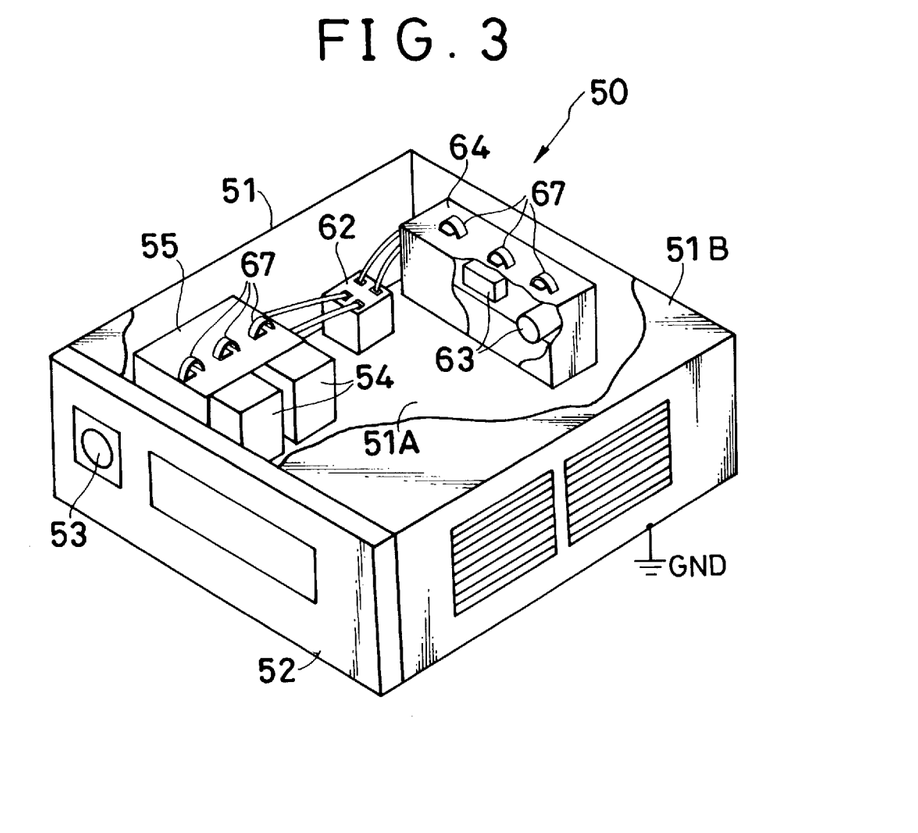
Fig. 3 is a perspective view of a second embodiment of a structure for eliminating the noise in a light source device for an electronic endoscope according to the present invention.

FIGS. 3 to 6 show a second embodiment of a structure for eliminating the noise in a light source device for an electronic endoscope according to the present invention. In FIGS. 3, 5(A) and 5(B), a light source device 50 is provided with a conductive box body 51, which is earthed to the ground (frame ground GND). A connector receptacle 53 for receiving a light guide connector of the electronic endoscope is provided on the front panel 52 of the box body 51.

Figure 6:
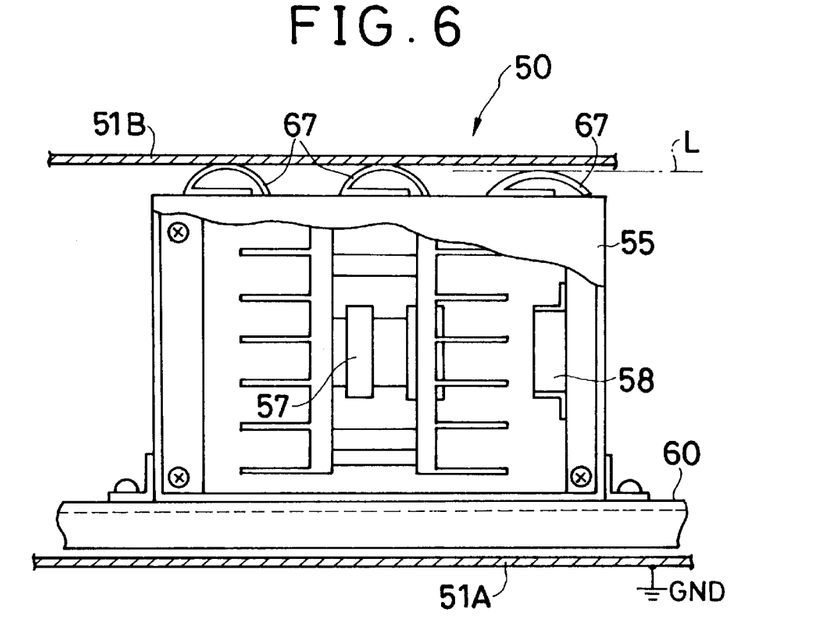
FIG. 6 is a side elevational view of the light source device shown in FIG. 3, explaining the lamp house portion and the interior thereof.

A lamp house 55 provided with a cooling fan 54 is disposed within the box body 51, and the lamp house 55 serves as a conductive shield case body. A xenon lamp 57 is provided in the lamp house 55, as shown in FIG. 6. The light of the xenon lamp 57 is radiated from a port 58 toward the connector receptacle 53. The lamp house 55 is fixed onto a metal support frame 60, by fixing screws, which is integrally fixed to the bottom surface 51A of the box body 51.

Figure 5A:
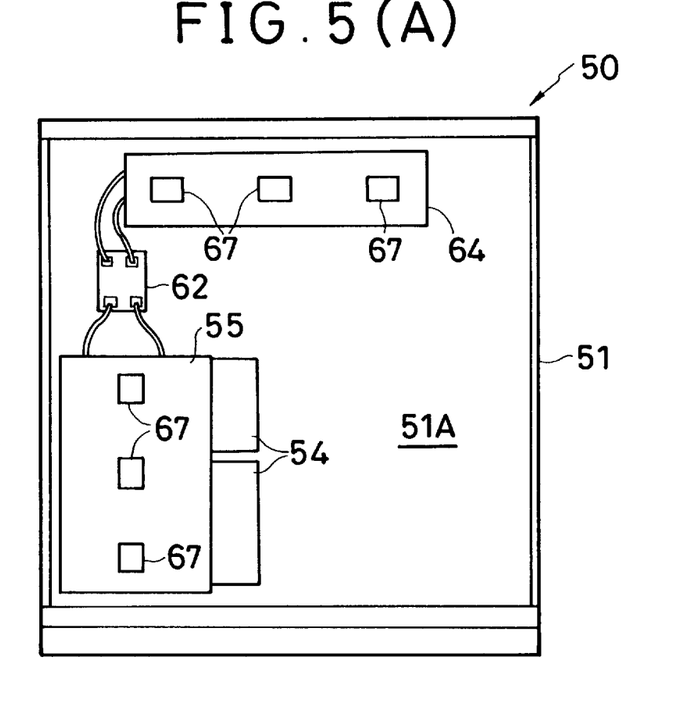
FIG. 5(A) is a top view of the light source device shown in FIG. 3 with the top plate removed therefrom.
Figure 5B:
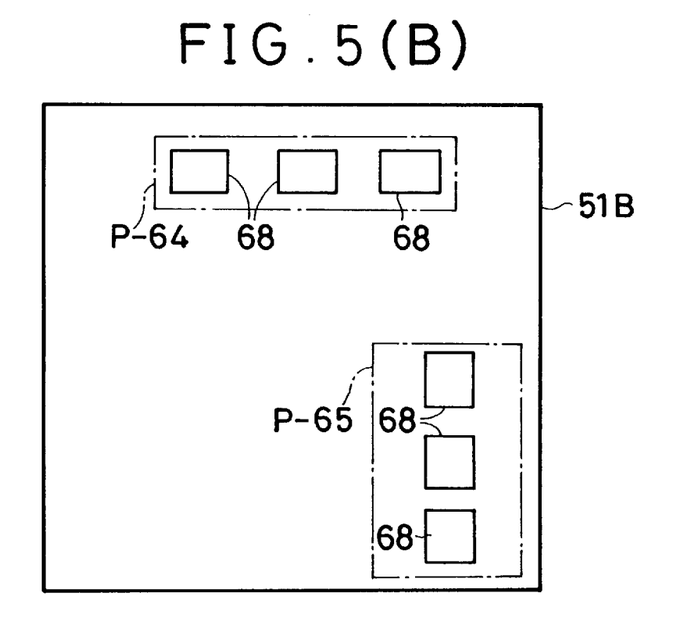
FIG. 5(B) shows the back surface of the top plate of the light source device shown in FIG. 3.

In FIGS. 3, 5(A) and 5(B), an igniter 62 is connected to the lamp house 55 (xenon lamp 57) through lead wires. and a lighting circuit 63 is connected to the igniter 62 through lead wires. In this embodiment, the outer periphery of the lighting circuit 63 is also covered with a case body 64 as a conductive shield body, thereby shielding the high-frequency noise produced by the switching current of the lighting circuit 63.

Figure 4:
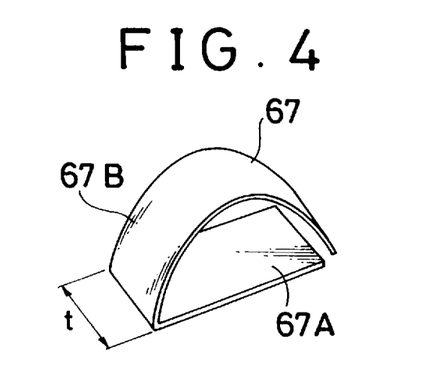
Fig. 4 is a perspective view of an EMI spring in the second embodiment shown in FIG. 3.

EMI springs 67 are disposed between the upper surfaces of the lamp house 55 and the case body 64 and the back surface of the top plate 51B of the box body 51 of the light source device 50. The EMI spring 67 is composed of a bottom sheet 67A and an elastic arch sheet 67B which is bent so as to be freely expanded and contracted in the vertical direction like a spring. By providing the bottom sheet 67A having a large width t, it is possible to have a large contact area. The EMI spring 67 is attached to each of the upper surfaces of the lamp house 55 and the case body 64 by an adhesive material attached to the back surface of the bottom sheet 67B (or by fixing screws).

With respect to the top plate 51B, although it is coated with an anticorrosive coating material or the like, the portions at which the EMI springs 67 are disposed are not coated. FIG. 5(B) shows the back surface of the top plate 51B. Maskings 68 are attached to the portion P-55 corresponding to the upper surface of the lamp house 55 and the portion P-64 corresponding to the upper surface of the case body 64. After the end of coating, the maskings 68 are removed. In this manner, it is possible to keep the masked portions conductive. Alternatively, it is possible to coat these portions with a conductive coating material.

FIG. 6 shows the second embodiment having the above-described structure with the EMI springs 67 disposed between the upper surfaces of the lamp house 55 and the back surface of the top plate 51B. According to this structure, the conductive upper surface of the lamp house 55 and the conductive back surface of the top plate 51B are electrically connected by the EMI springs 67, and the connecting area between the lamp house 55 and the box body 51 is large as compared with the case of connecting them by screws or the like. In addition, by using a plurality of EMI springs 67, it is possible to separate the upper portion at which noise current stores into several portions at predetermined intervals, thereby enhancing the noise eliminating efficiency.

Furthermore, by using a conductive elastic material such as the EMI spring 67, it is possible to cope well with the case in which the space between the upper surface of the lamp house 55 and the back surface of the top plate 51B is slightly different at a certain point, or the case in which the position of the top plate 51 changes due to a certain cause. For example, when something is placed on the upper surface of the light source device 50, the top plate 51B sags, as indicated by the chain line L in FIG. 6, but it is possible to maintain the contact between the lamp house 55 and the top plate 51B because the EMI spring 67 bends.

Although the EMI spring 67 is used as a conductive elastic material in the second embodiment, a conductive sponge which is expandable to a certain extend or the like can also be used.

As explained above, according to the second embodiment, since the case body 54 and the lamp house 55, and the box body 11 are maintained at the same potential by the conductive EMI springs 67, it is possible to eliminate the noise produced from the xenon lamp 57 and the noise produced from the lighting circuit 63.

Third Embodiment

Figure 7:
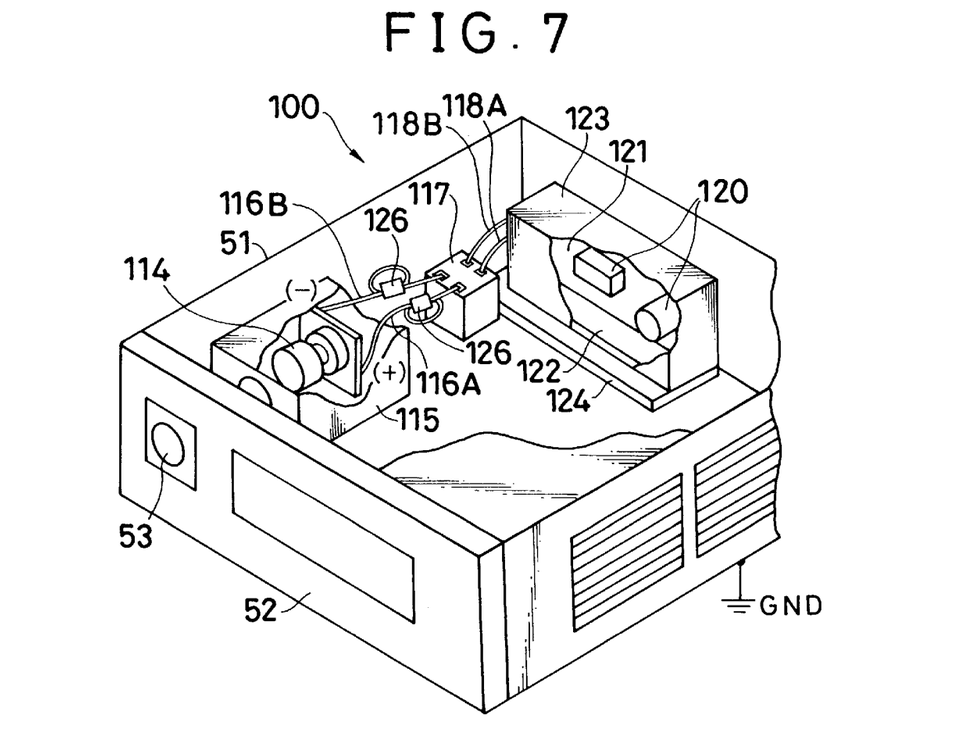
FIG. 7 is a perspective view of a third embodiment of a structure for eliminating the noise in a light source device for an electronic endoscope according to the present invention.
Figure 8:
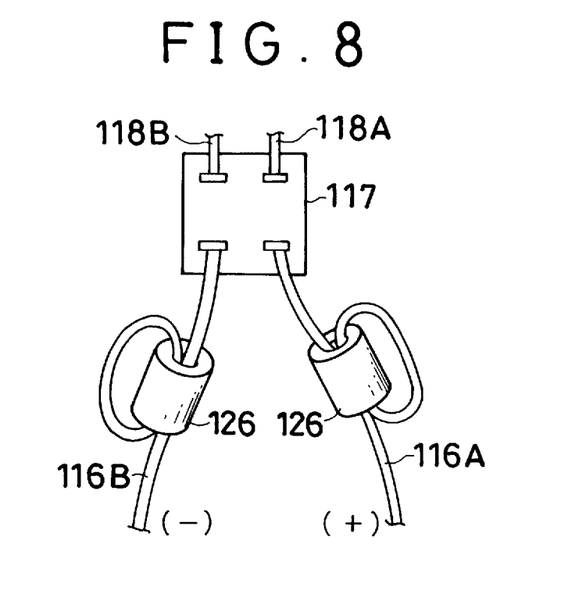
FIG. 8 shows the portion to which a ferrite core is attached in the third embodiment shown in FIG. 7.
Figure 9:
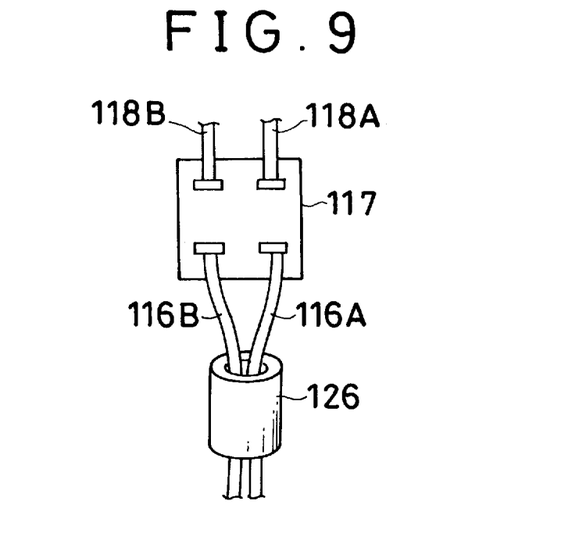
FIG. 9 shows another state in which a ferrite core is attached.

FIGS. 7 to 9 show a third embodiment of a structure for eliminating the noise in a light source device for an electronic endoscope according to the present invention. In FIG. 7, in a light source device 100, a conductive box body 111 is also earthed to the ground (frame ground GND). The box body 111 is provided therein with a lamp house 115 accommodating a xenon lamp 114.

A conductive wire (lead wire) 116A is connected to the anode and a conductive wire 116B is connected to the cathode of the xenon lamp 114. An igniter 117 is connected to the xenon lamp 114 through the conductive wires 116A, 116B. A switching circuit such as a transistor is provided in the lighting circuit 120, and a switching current is produced. The igniter 117 then discharges in accordance with the switching current and a high-voltage pulse current is supplied to the xenon lamp 114.

The lighting circuit 120 is fixed onto a metal support 122 through a substrate 121, and the entire portion of the lighting circuit 120 and the support 122 is covered with a case body 123 which serves as a conductive shield body. The support 122 is attached to the box body 111 through an insulating plate 124.

Separate ferrite cores 126 are provided on the two conductive wires 116A, 116B which connect the igniter 117 and the xenon lamp 114. The ferrite cores 126 are attached to the conductive wires 116A, 116B, for example, as shown in FIG. 8. In this example, the ferrite cores 126 are attached to the wires on the anode and cathode sides by passing the the respective wires through the ferrite cores 126 and looping back the wires so as to pass them again through the respective cores 126.

It is also possible to provide the ferrite core 126 by passing the wires 116A, 116B on the anode and cathode sides through the ferrite core 126, as shown in FIG. 9. However, when the ferrite core 126 is provided in this manner, since the distance between the wires 116A and 116B becomes short, the high-voltage pulses disturb, thereby exerting a deleterious influence on the control of the lighting operation. In addition, it may cause the dielectric breakdown of the wires 116A and 116B on the anode and cathode sides.

Accordingly, in the third embodiment, the ferrite cores 126 are disposed separately on the wires 116A and 116B on the anode and cathode sides so as to securely separate the wires 116A and 116B. These wires have a large diameter due to the necessity of transmitting a large current. Therefore, if the two wires 116A, 116B are passed through the ferrite core 126, as shown in FIG. 9, each wire can be passed therethrough only once. In contrast, in the case shown in FIG. 8, each wire can be passed through the ferrite core 126 twice. Since the impedance with respect to the noise current in the ferrite core 126 rises in proportion to the square of the number of turns, the noise eliminating effect is advantageously enhanced.

According to the ferrite core 126, the noise transmitted through the wires 116A, 116B on the anode and cathode sides is eliminated, and the generation of a high-frequency noise due to the switching current used by the lighting circuit 120, the high-voltage pulses produced by the igniter 117 and the high-frequency noise due to the discharge of the xenon lamp 114 is suppressed.

The ferrite core 126 may be disposed only on the wire 116A on the anode side, or they may also be disposed on the wires 118A and 118B on the anode and cathode sides between the igniter 117 and the lighting circuit 120.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A structure for eliminating noise in a light source device for an electronic endoscope, said structure comprising:

a lighting circuit for controlling the lighting operation of a light source;

a box body of said light source apparatus on which a support of said lighting circuit is disposed through an insulating plate; and a capacitor which has a predetermined withstand voltage and which is connected between said support of said lighting circuit and said box body so as to introduce the noise current produced by the switching operation of said lighting circuit from said support of said lighting circuit to the ground of said box body.

2. A structure for eliminating noise in a light source device for an electronic endoscope according to claim 1, further comprising a shield case body disposed around the outer periphery of said lighting circuit.

3. A structure for eliminating noise in a light source device for an electronic endoscope, said structure comprising:

a light source provided with a xenon lamp;

a conductive shield case body for accommodating said xenon lamp and/or a lighting circuit for said xenon lamp;

a conductive elastic material inserted between the outer peripheral surface of said shield case body and the inner peripheral surface of the conductive box body of said light source device so as to make electrical contact therewith and maintain said shield case body and said box body at the same potential.

4. A structure for eliminating noise in a light source device for an electronic endoscope according to claim 3, wherein said conductive elastic material includes a bottom sheet and a bendable arch sheet.

5. A structure for eliminating noise in a light source device for an electronic endoscope according to claim 3, wherein a plurality of said conductive elastic materials are disposed between the upper surface of said shield case body and the back surface of the top plate of said box body.

6. A structure for eliminating noise in a light source device for an electronic endoscope, said structure comprising:

a light source provided with a xenon lamp;

a lighting circuit for controlling the lighting operation of said light source;

a ferrite core for eliminating noise which is provided either on both a wire connecting the anodes and a wire connecting the cathodes of said lighting circuit and said light source or on only said wire connecting said anodes thereof and wherein said ferrite cores are provided on said wires on the anode and cathode sides separately.

* * * * *